(12) United States Patent
Ghare

(10) Patent No.: US 9,284,265 B1
(45) Date of Patent: *Mar. 15, 2016

(54) PREPARATION OF ORGANIC ACID SALTS OF CATIONIC SURFACTANTS

(76) Inventor: Vishwas Sadhu Ghare, Maharashtra (IN)

( * ) Notice: Subject to any disclaimer, the term of this patent is extended or adjusted under 35 U.S.C. 154(b) by 104 days.

This patent is subject to a terminal disclaimer.

(21) Appl. No.: 13/506,702

(22) Filed: May 10, 2012

Related U.S. Application Data

(63) Continuation-in-part of application No. 12/592,754, filed on Dec. 2, 2009, now Pat. No. 8,212,061.

(51) Int. Cl.
  *C07C 51/00* (2006.01)
  *C07C 235/86* (2006.01)

(52) U.S. Cl.
  CPC .................................... *C07C 235/86* (2013.01)

(58) Field of Classification Search
  CPC ...... C07C 51/412; C11D 13/04; C11D 13/02; C11D 13/20; A23K 1/164
  USPC .................................................. 554/51, 156
  See application file for complete search history.

(56) References Cited

U.S. PATENT DOCUMENTS

| | | | |
|---|---|---|---|
| 5,780,658 A | 7/1998 | Martinez-Pardo et al. | 554/51 |
| 7,074,447 B2 | 7/2006 | Bonaventura et al. | 426/321 |
| 7,087,769 B1 | 8/2006 | Contijoch Mestres et al. | 554/69 |
| 7,399,616 B2 | 7/2008 | Bonaventura et al. | 435/106 |
| 7,407,679 B2 | 8/2008 | Beltran et al. | 426/335 |
| 8,212,061 B1 * | 7/2012 | Ghare | 554/156 |
| 2008/0286427 A1 | 11/2008 | Urgell Beltran et al. | 426/323 |

FOREIGN PATENT DOCUMENTS

WO  WO 2007/014580 A1  8/2007 ............... A61K 8/44

* cited by examiner

*Primary Examiner* — Deborah D Carr
(74) *Attorney, Agent, or Firm* — Jack Matalon

(57) ABSTRACT

The invention pertains to a highly efficient process for preparing a very pure organic acid salt of a cationic surfactant derived from the condensation of a fatty acid with an esterified dibasic amino acid. The process involves the following steps:
  (a) providing a reaction mixture comprising a mineral acid salt of the cationic surfactant and an alkali and/or alkaline earth metal salt of the organic acid;
  (b) allowing the reaction between the mineral acid salt of the cationic surfactant and the alkali and/or alkaline earth metal salt of the salt to proceed until substantially all of the mineral acid salt of the cationic surfactant has been converted to the organic acid salt of the cationic surfactant; and
  (c) recovering the organic acid salt of the cationic surfactant from the reaction mixture.

20 Claims, No Drawings

PREPARATION OF ORGANIC ACID SALTS OF CATIONIC SURFACTANTS

CROSS-REFERENCE TO RELATED PATENT APPLICATION

This application is a continuation-in-part of utility application Ser. No. 12/592,754, filed Dec. 2, 2009 now U.S. Pat. No. 8,212,061.

FIELD OF THE INVENTION

The present invention relates to a highly efficient method for converting a mineral acid salt of a cationic surfactant into an organic acid salt of the cationic surfactant. The resultant organic acid salt is very useful for incorporation into a wide variety of products, e.g., food products, pharmaceuticals, cosmetics, etc. to thereby inhibit the proliferation of different types of microorganisms such as bacteria, fungi and yeasts resulting in an increase in the useful life of such products, particularly perishable food products.

BACKGROUND OF THE INVENTION

Mineral acid salts of cationic surfactants derived form the condensation of fatty acids and esterified dibasic amino acids and their use for the preservation of foodstuffs are known in the prior art—see, e.g., U.S. Pat. Nos. 5,780,658, 7,087,769 and 7,407,679. A useful cationic surfactant is the ethyl ester of lauramide-arginine (hereinafter referred to as the ethyl ester of $N^\alpha$-lauroyl-L-arginine); such ester is also referred to herein by the term "LAE". The anions of such mineral acid salts are typically $Br^-$, $Cl^-$ or $HSO_4^-$, with the most typical being $Cl^-$.

It is also known in the prior art to prepare organic acid salts rather than the mineral acid salts of the cationic surfactants. WO 2007/014580 discloses that such organic acids may be, e.g., citric acid, lactic acid, acetic acid, fumaric acid, maleic acid, gluconic acid, propionic acid, benzoic acid, carbonic acid, glutamic acid or other amino acids, lauric acid and fatty acids such as oleic acid and linoleic acid.

It has been found that the organic acid salts of the cationic surfactants, rather than the mineral acid salts of the cationic surfactants, are especially useful for the preservation of foodstuffs. However, the process for preparing the organic acid salts disclosed in WO 2007/014580 leaves a lot to be desired. The yields are poor and moreover, the product is impure. For example, in the case of LAE being converted from the monohydrochloride salt to the acetate salt, the product is contaminated with a significant amount of the byproduct $N^\alpha$-lauroyl-arginine ("LAS") acetate.

OBJECTS OF THE INVENTION

It is an object of the invention to provide a highly efficient process for the preparation of organic acid salts of cationic surfactants.

It is a further object of the invention to provide a process resulting in the production of organic acid salts of cationic surfactants in exceptionally high yields.

It is yet an additional object of the invention to provide a process resulting in the production of exceptionally pure organic acid salts of cationic surfactants.

These and other objects have been met by this invention whose details are set forth below.

DETAILS OF THE INVENTION

The process of the invention pertains to the preparation of an organic acid salt of a cationic surfactant derived from the condensation of a fatty acid with an esterified dibasic amino acid comprising the steps of:
   (a) providing a reaction mixture comprising a mineral acid salt of the cationic surfactant and an alkali and/or alkaline earth metal salt of the organic acid;
   (b) allowing the reaction between the mineral acid salt of the cationic surfactant and the alkali and/or alkaline earth metal salt of the organic acid salt to proceed until substantially all of the mineral acid salt of the cationic surfactant has been converted to the organic acid salt of the cationic surfactant; and
   (c) recovering the organic acid salt of the cationic surfactant from the reaction mixture.

The process of the invention may be carried out in two modes: In a first mode, the reaction between the mineral acid salt of the cationic surfactant and the alkali and/or alkaline earth metal salt of the organic acid takes place "neat", i.e., the mineral acid salt of the cationic surfactant is present in the reaction mixture in a molten state and a diluent is not present in the reaction mixture. In the first mode, the mineral acid salt of the cationic surfactant is heated, e.g., to a temperature of about 60-75° C., in order to melt it and the alkali and/or alkaline earth metal salt of the organic acid is added to the molten mass, with agitation.

The reaction between the mineral acid salt of the cationic surfactant and the alkali and/or alkaline earth metal salt of the organic acid is exothermic. When the temperature of the reaction mixture remains stable, the reaction is complete, i.e., substantially all (i.e., at least about 95%) of the mineral acid salt of the cationic surfactant has been converted into the organic acid salt of the cationic surfactant. Another indication that the reaction is complete is that the volume of solids in the reaction flask decreases since the volume of the by-product of the reaction, i.e., the alkali and/or alkaline earth metal halide salt, is less than the volume of the desired product, i.e. the organic acid salt of the cationic surfactant. Typically, a reaction temperature of about 20 to about 100° C., preferably 40-80° C., and a residence time of about 0.5 to about 10 hours, preferably 1-6 hours, are required for completion of the reaction.

In order to insure that the reaction is complete after step (b) of the process has been carried out, a diluent of the type described below is preferably added to the reaction mass before commencing step (c) of the process and agitation is continued for a period of about 0.5 to about 4 hours at a temperature of 40-80° C.

In the second mode of carrying out the process of the invention, the reaction mixture in step (a) will initially comprise the mineral acid salt of the cationic surfactant and a diluent of the type described below. The initial reaction mixture is stirred for several minutes and heated to a temperature of about 40 to about 80° C. Thereafter, the alkali metal and/or alkaline earth metal salt of the organic acid is slowly added with agitation to the reaction mixture. Here again, an exothermic reaction takes place, but the temperature rise is less (than when the reaction is conducted "neat"), due to the moderating presence of the diluent. When the temperature of the reaction mixture remains stable, the reaction is complete and substantially all (i.e., at least about 95%) of the mineral acid salt of the cationic surfactant has been converted into the organic acid salt of the cationic surfactant. Another indication that the reaction is complete is that the volume of solids in the reaction flask decreases since the volume of the by-product of the reaction, i.e., the alkali and/or alkaline earth metal halide salt, is less than the volume of the desired product, i.e., the organic acid salt of the cationic surfactant. Typically, a reaction temperature of about 20 to about 100° C., preferably 40-80° C., and a residence time of about 0.5 to about 10 hours, preferably 1-6 hours, are required for completion of the reaction for completion of the process in the second mode.

Step (c) of the process of the invention is readily accomplished by filtering the reaction mixture while it is hot. In order to insure that no organic acid salt of the cationic surfactant is entrained in the by-product precipitate (i.e., the alkali and/or alkaline earth metal halide salt), the precipitate may be washed one or more times with additional quantities of the diluent. The diluent is then distilled off from the filtrate (plus any washings) under vacuuo, e.g., at 40-60° C. and 40-60 mm Hg.

Regardless of which mode of the process of the invention is practiced, the yield of the product will typically be in the range of 95-99% of theory and the purity of the product will be typically be in the range of 98-99%.

In general, the diluent is utilized in the reaction mixture in a ratio of about 2 to about 10 w/v, preferably 3 to 6 w/v, based on the weight of the mineral acid salt of the cationic surfactant.

In general the diluent will be one that has a Hildebrand Solubility Parameter in the range of about 7 to about 17. Toxic diluents such as ethylene glycol should be avoided since the end product, i.e. the organic acid salt of the surfactant, is primarily to be used for products such as foods, pharmaceuticals and cosmetics. Accordingly, diluents that are on the FDA GRAS ("Generally Recognized As Safe") list having the requisite Hildebrand Solubility Parameter of about 7 to about 17 are preferred.

Useful diluents include $C_1$-$C_4$ straight chain alcohols, $C_1$-$C_4$ branched chain alcohols, $C_1$-$C_4$ straight chain esters of $C_1$-$C_8$ monobasic organic acids, branched chain esters of $C_1$-$C_8$ monobasic organic acids, $C_3$ and higher glycols, $C_3$ and higher glycol ethers, $C_3$ and higher hydroxy alcohols, $C_3$ and higher ketones, $C_4$ and higher hydroxy ketones, $C_4$ and higher aliphatic ethers, $C_4$ and higher cyclic ethers, $C_5$ and higher straight chain alkanes, $C_5$ and higher branched chain alkanes, $C_5$ and higher cyclic alkanes and mixtures thereof.

Representative examples of suitable diluents having the requisite Hildebrand Solubility Parameter are set forth in the following table:

| Diluent | Hildebrand Solubility Parameter |
| --- | --- |
| methanol | 14.28 |
| ethanol | 12.92 |
| n-propanol | 11.67 |
| 2-propanol | 11.6 |
| n-butanol | 11.3 |
| 2-methoxyethanol | 11.65 |
| propylene glycol | 16.3 |
| glycerol | 16.9 |
| ethyl acetate | 9.1 |
| n-butyl acetate | 8.7 |
| amyl acetate | 8.5 |
| diacetone alcohol | 10.18 |
| ethyl ether | 7.62 |
| tetrahydrofuran | 9.52 |
| acetone | 9.77 |
| methyethylketone | 9.77 |
| butyl cellosolve | 10.24 |
| n-heptane | 7.24 |
| n-hexane | 7.24 |
| cyclohexane | 8.18 |

The particularly preferred diluents to be employed in step (a) are ethyl acetate and propylene glycol. It is also preferred that the reaction mixture not contain any water.

The mineral acid salt of the cationic surfactant may be the hydrochloride, the hydrobromide, the nitrate, the nitrite, the phosphate, the phosphite, the sulfate and the like. The cationic surfactant may be any of those known in the prior art, such as an $N^\alpha$-($C_1$-$C_{22}$) alkanoyl di-basic amino acid ($C_1$-$C_{22}$) alkyl ester. The preferred cationic surfactants are $N^\alpha$-lauroyl-L-arginine ethyl ester, $N^\alpha$-lauroyl-L-histidine ethyl ester and $N^\alpha$-lauroyl-L-tryptophan ethyl ester.

Typically, the alkali and/or alkaline earth metal salt of the selected organic acid will be employed in a molar amount of about 1 to about 1.5 moles, preferably 1 to 1.3 moles, per mole of the mineral acid salt of the selected cationic surfactant. The alkali metal may be, e.g., sodium, potassium, lithium, etc., while the alkaline earth metal may calcium, magnesium, etc. Preferably, the salt of the organic acid is the sodium salt.

The organic acid may be a carboxylic acid such as acetic, benzoic, butyric, capric, caproic, caprylic, citric, formic, fumaric, gluconic, glyceric, glycolic, heptanoic, lactic, lauric, linoleic, maleic, malic, myristic, nonanoic, oleic, palmitic, propionic, salicyclic, sorbic, stearic, tartaric, undacanoic, undecylenic or valeric. Preferred organic acids are acetic, citric, lactic and lauric. The particularly preferred organic acid is acetic acid.

The following non-limiting examples shall serve to illustrate the various embodiments of this invention. Unless otherwise indicated, all amounts and percentages are on a weight basis.

Example 1

A 1-liter flask was set up with a stirrer, thermometer, heating mantle, condenser and a vacuum distillation unit. To the flask with stirring were added 42 g (0.1 mole) LAE hydrochloride and 350 g of distilled water. Thereafter, 9.5 g (0.115 mole) of sodium acetate were added and the reaction mixture was stirred for six hours at a temperature of 20-25° C. It was noted that some white precipitate was present. Thereafter, 300 g of ethyl acetate were added and the mixture was stirred for two hours at a temperature of 20-25° C.

The stirring was stopped and the mixture was poured into a separatory funnel and the top product phase was removed (it was noted that a small amount of white precipitate was present in the product phase). The ethyl acetate solvent was distilled off at a temperature of 75-80° C. under 50-60 mm Hg vacuum. The results were as follows:

| Product weight | 32 g |
| --- | --- |
| % sodium chloride | 2.1% |
| % LAS | 1.9% |
| % LAE hydrochloride | 14.1% |
| % LAE acetate | 82.0% |
| % Yield | 60.0% |

It was concluded that the use of water in the reaction mixture may be detrimental since the yield of the LAE acetate was only 60% and the product was contaminated with by-products and unreacted LAE hydrochloride. However, as may be seen from Example 9 set forth below, it is possible to prepare pure product in a high yield using water as the diluent.

Example 2

Example 1 was repeated, except that after the addition of the sodium acetate, the reaction mixture was heated to 75-80° for six hours (white precipitate was again present in the reaction mixture). The results were as follows:

| Product weight | 35 g |
|---|---|
| % sodium chloride | 2.4% |
| % LAS | 21.0% |
| % LAE hydrochloride | 11.0% |
| % LAE acetate | 55.4% |
| % Yield | 44.6% |

It was concluded that the use of water in the reaction mixture coupled with the elevated reaction temperature may result in poor product yield and further that the product had a relatively high level of contamination from by-products and unreacted LAE hydrochloride.

Example 3

This example was carried out using the same equipment set-up as is described in Example 1. 42 g (0.1 mole) of LAE hydrochloride and 300 g of ethyl acetate were placed in the reaction flask and stirred. Thereafter, 9.5 g (0.115 mole) of sodium acetate were added with stirring. The reaction mixture was then heated, while stirring, to 50° C. and maintained at such temperature for six hours. The reaction mixture was then allowed to come to room temperature and filtered to remove the insoluble precipitate. The insoluble precipitate was then washed with 50 g of ethyl acetate to remove any product that may have been entrained in the precipitate. The ethyl acetate filtrate fractions were then combined and the ethyl acetate was distilled off at 75-80° C. and 40 to 50 mm Hg vacuum.

The results were as follows:

| Product weight | 38 g |
|---|---|
| % sodium chloride | 0.4% |
| % LAE hydrochloride | 3.1% |
| % LAE acetate | 95.5% |
| % Yield | 82.0% |

The product had a melting point of 77-79° C.

The results of Example 3 demonstrate that the process of the invention using ethyl acetate as the diluent, a reaction temperature of 50° C. and a reaction time of six hours, is highly efficient and product with high purity and in high yield can be obtained.

Example 4

Example 3 was repeated using a reaction temperature of 75-80° C. and a reaction time of four hours. The results were as follows:

| Product weight | 43.1 g |
|---|---|
| % LAE hydrochloride | 0.7% |
| % LAE acetate | 98.2% |
| % Yield | 95.5% |

The product had a melting point of 80-82° C.

The results of Example 4 demonstrate that the process of the invention using ethyl acetate as the diluent, a reaction temperature of 75-80° C. and a reaction time of four hours can produce product with excellent purity and excellent yield.

Example 5

Example 4 was repeated except that the reaction time was six hours rather than four hours. The results were as follows:

| Product weight | 44.1 g |
|---|---|
| % LAE hydrochloride | 0.32% |
| % LAE acetate | 99.2% |
| % Yield | 98.5% |

The product had a melting point of 81-83° C.

The results of Example 5 demonstrate that the process of the invention using ethyl acetate as the diluent, a reaction temperature 75-80° C. and a reaction time of six hours can produce product with exceptional purity and exceptional yield.

Example 6

This example was carried out using the same equipment set-up as is described in Example 1. 42 g (0.1 mole) of LAE hydrochloride were added to the flask and heated to 65-70° C. to melt it. Thereafter, 23.34 g (0.105 mole) of powdered sodium laurate were added to the flask with agitation (the reaction was exothermic—the temperature rose to 85° C.). The reaction mixture was maintained at 80-85° C. for 30 minutes to complete the reaction. Subsequently, 300 g of ethyl acetate were added to the flask at 80° C. and the contents of the flask were agitated and held at 75° C. for 30 minutes. The contents of the flask were then filtered hot to remove the by-product salt precipitate. The by-product precipitate was washed with additional ethyl acetate diluent to remove any entrained product. The ethyl acetate diluent fractions were then removed under vacuuo at 70-75° C. and 50-60 mm Hg. The yield of the product was 57.31 g (96.5% yield). The HPLC assay of the product was as follows:

| % LAE Laurate | 98.5% |
|---|---|
| % LAS | 0.8% |
| % Lauric Acid | 0.4% |

Example 7

Example 6 was repeated using 42 g of LAE hydrochloride which was heated to 65-70° C. to melt it. Thereafter, 22.5 g (0.105 mole) of powdered monosodium citrate were added with agitation (the reaction was exothermic—the temperature rose to 82° C.). The reaction mixture was maintained at 80-85° C. for 30 minutes to complete the reaction. Subsequently, 300 g of ethyl acetate were added to the flask at 80° C. and the contents of the flask were agitated and held at 75°

C. for 30 minutes. The contents of the flask were then filtered hot to remove the by-product salt. The by-product precipitate was washed with additional ethyl acetate diluent to remove any entrained product. The ethyl acetate diluent fractions were then removed under vacuuo at 70-75° C. and 50-60 mm Hg. The yield of the product was 57.1 g (97.8% yield). The HPLC assay of the product was as follows:

| | |
|---|---|
| % LAE Citrate | 98.5% |
| % LAS | 0.6% |
| % Citric Acid | 0.2% |

Example 8

Example 6 was repeated using 42 g of LAE hydrochloride which was heated to 65-70° C. to melt it. Thereafter, 11.8 g (0.105 mole) of powdered sodium lactate were added with agitation (the reaction was exothermic—the temperature rose to 83° C.). The reaction mixture was maintained at 75-85° C. for 30 minutes to complete the reaction. Subsequently, 300 g of ethyl acetate were added to the flask at 75° C. and the contents of the flask were agitated and held at 75° C. for 30 minutes. The contents of the flask were then filtered hot to remove the by-product salt. The ethyl acetate diluent was then removed under vacuuo at 70-75° C. and 50 mm Hg. The yield of the product was 46.5 g (96.7% yield). The HPLC assay of the product was as follows:

| | |
|---|---|
| % LAE Lactate | 98.5% |
| % LAS | 0.6% |
| % Lactic Acid | 0.45% |

Example 9

Although it is stated above that water preferably not be present in the reaction mixture, it has been found that it is nevertheless possible to use water as a diluent for some applications wherein it is desired to avoid the use of an organic diluent.

A 1-liter flask was set up with a stirrer, thermometer, heating mantle, condenser and a vacuum distillation unit. The following ingredients were added to the flask: lauric acid, 20 g (0.1 mole); water, 400 g; sodium hydroxide pellets, 4 g (0.1 mole); LAE hydrochloride, 42.1 g (0.1 mole); sodium chloride, 95 g.

The water was placed in the flask and thereafter the sodium hydroxide was added and the mixture was stirred to form a solution. Thereafter, the solution was heated to 40° C. and the lauric acid was added with stirring. The resultant solution was then heated to 45° C., thereby resulting in the sodium salt of lauric acid. The LAE hydrochloride was then added at 45° C., and the temperature rose to 50° C. (exothermic reaction). The reaction mixture was stirred for one hour at 45-50° C. and thereafter, the reaction mixture was heated to 80° C. The sodium chloride was then added with stirring in order to saturate the aqueous phase, thereby forcing the product out of the aqueous phase. The top oil (product) phase was removed and dried under vacuum at 65-70° C. The results were as follows:

| | |
|---|---|
| Product weight: | 57 g (theory is 58.5 g) |
| % Yield: | 94% |
| % Unreacted LAE•HCl: | 1.4% |
| Purity (HPLC assay) | 96.5% |

The results achieved with this example show that it is possible to use water as a diluent in the reaction and nevertheless obtain quite pure LAE laurate with a very good yield.

The foregoing examples are provided for illustrative purposes only and should not be construed as representing any limitations on the scope of the invention. The scope of the invention is defined by the claims which follow.

What is claimed is:

1. A process for the preparation of an organic acid salt of a cationic surfactant derived from the condensation of a fatty acid with an esterified dibasic amino acid comprising the steps of:
   (a) providing a reaction mixture comprising a mineral acid salt of the cationic surfactant and an alkali or alkaline earth metal salt of the organic acid;
   (b) allowing the reaction between the mineral acid salt of the cationic surfactant and the alkali and/or alkaline earth metal salt of the organic acid salt to proceed until substantially all of the mineral acid salt of the cationic surfactant has been converted to the organic acid salt of the cationic surfactant; and
   (c) recovering the organic acid salt of the cationic surfactant from the reaction mixture.

2. The process of claim 1 wherein the cationic surfactant comprises an $N^{\alpha}$-($C_1$-$C_{22}$) alkanoyl di-basic amino acid ($C_1$-$C_{22}$) alkyl ester.

3. The process of claim 2 wherein the cationic surfactant comprises an ester selected from the group consisting of $N^{\alpha}$-lauroyl-L-arginine ethyl ester, $N^{\alpha}$-lauroyl-L-histidine ethyl ester and $N^{\alpha}$-lauroyl-L-tryptophan ethyl ester.

4. The process of claim 3 wherein the cationic surfactant comprises $N^{\alpha}$-lauroyl-L-arginine ethyl ester.

5. The process of claim 1 wherein the mineral acid salt is selected from the group consisting of the hydrochloride, hydrobromide, nitrate, nitrite, phosphate, phosphite and sulfate.

6. The process of claim 1 wherein the alkali or alkaline earth metal salt of the organic acid is employed in a molar amount of about 1 to about 1.5 moles per mole of the mineral acid salt.

7. The process of claim 1 wherein the alkali metal comprises sodium.

8. The process of claim 1 wherein step (b) is carried out at a temperature in the range of about 20 to about 100° C. for a period of time of about 0.5 to about 10 hours.

9. The process of claim 1 wherein step (a) is carried out in the absence of any diluent and the mineral acid salt is present in the reaction mixture in a molten state.

10. The process of claim 1 wherein a diluent is present in the reaction mixture.

11. The process of claim 10 wherein the mineral acid salt and the diluent are present in the reaction mixture in a ratio of about 2 to about 10 w/v, based on the weight of the mineral acid salt.

12. The process of claim 10 wherein the diluent comprises water.

13. The process of claim 10 wherein the diluent has a Hildebrand Solubility Parameter in the range of about 7 to about 17.

14. The process of claim 10 wherein the diluent is selected from the group consisting of $C_1$-$C_4$ straight chain alcohols, $C_1$-$C_4$ branched chain alcohols, $C_1$-$C_4$ straight chain esters of $C_1$-$C_8$ monobasic organic acids, branched chain esters of $C_1$-$C_8$ monobasic organic acids, $C_3$ and higher glycols, $C_3$ and higher glycol ethers, $C_3$ and higher hydroxy alcohols, $C_3$ and higher ketones, $C_4$ and higher hydroxy ketones, $C_4$ and higher aliphatic ethers, $C_4$ and higher cyclic ethers, $C_5$ and higher straight chain alkanes, $C_5$ and higher branched chain alkanes, $C_5$ and higher cyclic alkanes and mixtures thereof.

15. The process of claim 14 wherein the diluent comprises an alcohol selected from the group consisting of ethanol, n-propanol, isopropanol and n-butanol.

16. The process of claim 13 wherein the diluent comprises an ester selected from the group consisting of ethyl acetate, methyl acetate, n-butyl acetate and ethyl formate.

17. The process of claim 13 wherein the diluent is selected from the group consisting of ethyl acetate and propylene glycol.

18. The process of claim 1 wherein the organic acid is selected from the group consisting of acetic acid, benzoic acid, butyric acid, capric acid, caproic acid, caprylic acid, citric acid, formic acid, fumaric acid, gluconic acid, glyceric acid, glycolic acid, heptanoic acid, lactic acid, lauric acid, linoleic acid, maleic acid, malic acid, myristic acid, nonanoic acid, oleic acid, palmitic acid, propionic acid, salicyclic acid, sorbic acid, stearic acid, tartaric acid, undacanoic acid, undecylenic acid and valeric acid.

19. The process of claim 16 wherein the organic acid is selected from the group consisting of acetic acid, citric acid, lactic acid and lauric acid.

20. The process of claim 17 wherein the organic acid comprises acetic acid.

* * * * *